United States Patent [19]

Gregory

[11] 4,367,743

[45] Jan. 11, 1983

[54] SELF-PRESSURIZING CRYOGENIC APPARATUS AND METHOD

[75] Inventor: Harold D. Gregory, West Covina, Calif.

[73] Assignee: Virginia M. Gregory, West Covina, Calif.

[21] Appl. No.: 218,531

[22] Filed: Dec. 22, 1980

Related U.S. Application Data

[60] Continuation of Ser. No. 936,909, Aug. 25, 1978, abandoned, which is a division of Ser. No. 688,962, May 24, 1976, abandoned.

[51] Int. Cl.$^3$ .............................................. A61B 17/36
[52] U.S. Cl. .................................. 128/303.1; 128/400; 62/50; 62/514 JT
[58] Field of Search ..................... 62/293, 514 JT, 50, 62/51; 128/303.1, 399, 400, 401; 222/3, 4

[56] References Cited

U.S. PATENT DOCUMENTS

| | | | |
|---|---|---|---|
| 2,645,097 | 7/1953 | Posch | 128/303.1 |
| 3,272,203 | 9/1966 | Chato | 128/303.1 |
| 3,651,813 | 3/1972 | Bryne | 128/303.1 |
| 3,696,813 | 10/1972 | Wallach | 128/303.1 |
| 3,924,628 | 12/1975 | Droegemueller et al. | 128/303.1 |
| 4,043,341 | 8/1977 | Tromovitch | 128/303.1 |

FOREIGN PATENT DOCUMENTS

| | | | |
|---|---|---|---|
| 2060422 | 6/1972 | Fed. Rep. of Germany | 128/303.1 |

*Primary Examiner*—Kyle L. Howell
*Assistant Examiner*—Daniel P. Burke
*Attorney, Agent, or Firm*—Sellers and Brace

[57] ABSTRACT

Apparatus and method for dispensing a jet of cryogenic coolant selectively in single gaseous phase and in dual gaseous and finely divided liquid phase from a self-pressurizing source of heat saturated liquid coolant. The coolant is stored under constant pressure and in a heat-saturated condition and, when needed, is partially expanded into an expansion chamber equipped with a coolant jetting orifice and a venting orifice regulatable to control coolant flow from the jetting orifice in single or dual phase. The liquid coolant is conveniently stored in a hand-held dewar flask equipped with a pressure relief valve and utilizing a relatively long, small bore passage as the coolant jetting orifice.

44 Claims, 4 Drawing Figures

U.S. Patent   Jan. 11, 1983   4,367,743
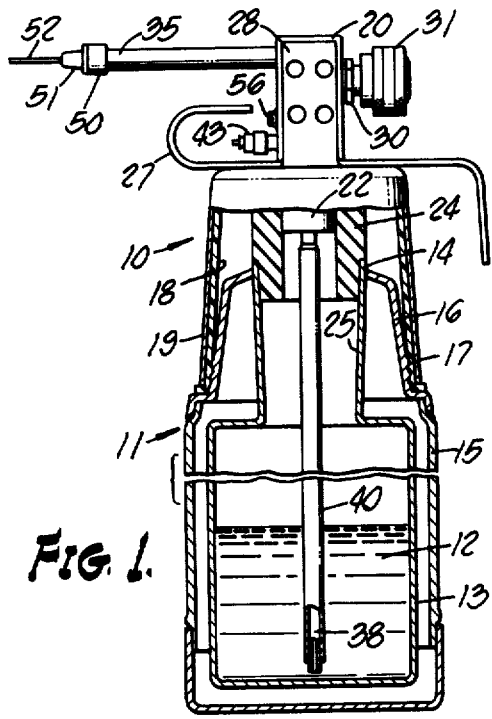
FIG. 1.
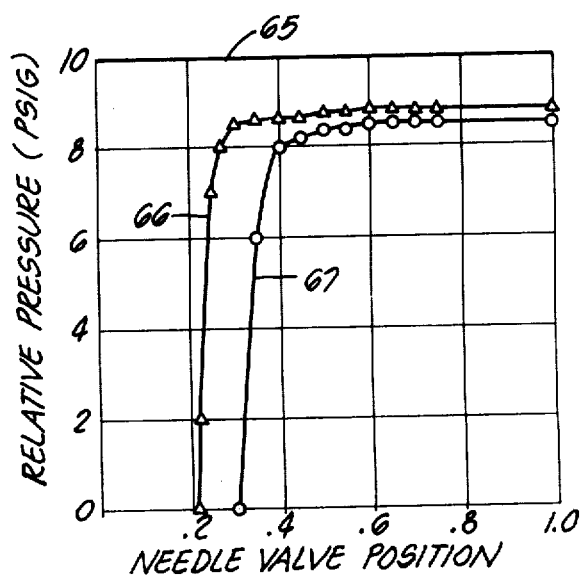
FIG. 4.
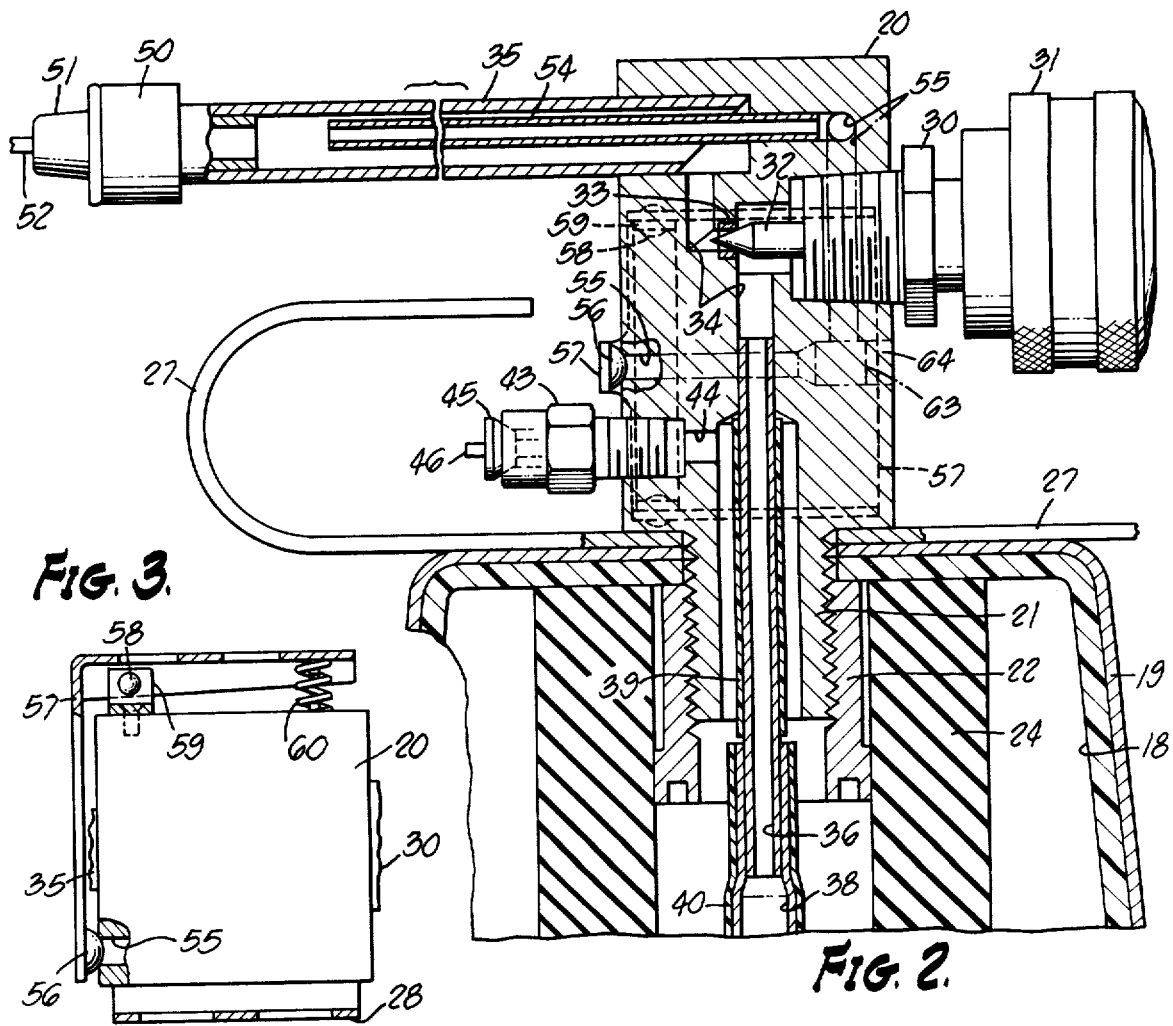
FIG. 3.
FIG. 2.

SELF-PRESSURIZING CRYOGENIC APPARATUS AND METHOD

This application is a continuation of my application for U.S. Letters Patent Ser. No. 936,909, filed Aug. 25, 1978, entitled SELF-PRESSURIZING CRYOGENIC APPARATUS AND METHOD, now abandoned, which application is a division of my application for U.S. Letters Patent. Ser. No. 688,962, filed May 24, 1976, now abandoned.

This invention relates to cryogenic apparatus and more particularly to simply constructed, hand-held means for dispensing a jet of cryogenic coolant onto an area to be necrotized from a self-pressurizing source of heat saturated liquid coolant having a boiling point below $-100°$ C.

BACKGROUND OF THE INVENTION

Equipment for dispensing a cryogenic liquefied gas onto a surface or object to be sharply cooled has been proposed heretofore. These are designed to utilize liquefied gas such as helium, nitrogen, oxygen, air, carbon dioxide, etc., stored in a suitable container. The liquid coolant is supplied therefrom to a dispensing port or nozzle in various ways including applying heat electrically or otherwise to the coolant to vaporize the liquid. Other designers pressurize the storage container to produce coolant flow by introducing air under pressure into the storage container while other designers provide the storage container with a normally open vent which is closed to initiate coolant flow whereby the vapor pressure which develops within the container produces a flow of coolant to the dispensing nozzle. The pressure build-up is slow and uncertain and varies widely depending on the volume of the vapor space and the quantity of liquid coolant in the storage chamber, the rate of heat leakage into the container and other factors.

One category of prior cryogenic devices dispenses a jet of coolant vapor directly onto the area to be cooled whereas those of another category confine the stream of coolant vapor to a flow passage typically provided with a return bend sector formed of excellent heat conductive material and venting to the atmosphere at a remote point. The heat conducting member can be placed close to or in contact with the surface to be cooled without risking direct contact of the gas coolant with that surface.

It has been recognized that it would be advantageous to deliver coolant in liquid phase onto or in close proximity to the area to be sharply cooled in order to utilize the latent heat or vaporization of the coolant as it changes to the gas phase. However, this presents numerous serious problems which have not been resolved prior to this invention. Foremost among these problems is control of the liquid coolant delivered and the amount of cooling provided. It is manifestly not feasible to deliver even a minute stream of liquid coolant onto living tissue. Not only is the cooling capacity of liquid coolant very great but, upon entering the atmosphere, becomes rapidly superheated with resultant vigorous boiling and uncontrolled dispersal.

Attempts have been made to create a spray of liquefied coolant particles of which can be dispensed directly onto the area to be necrotized. However, the equipment heretofore provided for this purpose is subject to many shortcomings and disadvantages including instability and erratic coolant flow, inability to form a stable, small diameter jet, fluctuating spurts of the coolant jet, time delay and waste involved in establishing a coolant jet, continuing change in the rate of flow, the highly inefficient use of a given charge of liquid coolant, and the need for recharging a hand-held reservoir several times a day.

SUMMARY OF THE INVENTION

To avoid the numerous shortcomings and disadvantages of prior cryogenic equipment, there is provided by this invention a self-pressurizing, self-stabilizing source of heat saturated liquid coolant. This coolant may be stored either in a stationary large capacity reservoir or a readily portable hand-held dewar flask. Such a flask having a capacity of approximately one pint of liquid is found adequate for seven to eight hours of normal usage without recharging, yet is so small and lightweight to be grasped in the hand and readily manoeuvred to meet operating requirements. The liquid coolant is automatically maintained at a predetermined uniform pressure by a pressure relief valve and, in consequence, the liquid is in continuous readiness for dispensing in a stable heat saturated condition. When open, a coolant flow control valve permits the coolant to flow into an expansion chamber equipped with a relatively long small bore outlet nozzle or orifice and normally open venting orifice cooperating with the outlet or coolant jetting orifice to limit the pressure differential across the flow control valve to a fraction of the pressure in the supply chamber. This pressure differential greatly limits the flashing of coolant into vapor. Additionally, and by properly proportioning the sizes of the outlet and venting orifices and the regulation of the latter, the invention apparatus is instantly self-stabilizing and operable to dispense either a needle-like jet of coolant in a dual phase of fine liquid particles and gas, or a jet of gaseous phase coolant depending upon whether gaseous coolant is vented from the venting orifice. The increased velocity imparted to the jet owing to the flashing of some superheated liquid into gas aids very substantially in increasing the "chill-factor" and thereby the effectiveness and efficiency of the device. For example, when using liquid nitrogen as the coolant, the temperature of this coolant in gas phase when dispensed from the nozzle of this invention is somewhat about 32° F. whereas the temperature of the issuing jet of dual phase coolant containing superheated liquid coolant is at least $-300°$ F. Further lowering of the temperature known as the "chill-factor" results as the rapidly flowing jet of particles of liquid coolant flash into the gaseous phase.

If the venting passage is open a portion of the coolant which is flashed into gas is bled from the expansion chamber and the resulting small drop of pressure in the expansion chamber converts the jet discharge substantially instantly from single to dual phase constituency without need for adjusting the flow control valve. Likewise, the jet discharge is converted instantly back to single phase by closing the venting orifice. Partial closing of the venting orifice merely varies the relative proportions of gas and liquid in the jet.

The stability of the device is enhanced by insulating the liquid flow tube extending between the coolant supply and the expansion chamber. This avoids reliquefication of a portion of the coolant vapor in the upper portion of the dewar during a dispensing cycle where a dispensing operation occurs before a new charge of coolant has become fully heat saturated.

Accordingly, it is a primary object of this invention to provide a self-pressurizing, self-stabilizing cryogenic device selectively operable to dispense a jet of single-phase or dual phase coolant having a boiling point below −100° C.

Another object of the invention is the provision of a unique method and apparatus for dispensing a jet of cryogenic coolant from a heat saturated uniformly pressurized source thereof and which is quickly convertible between single phase gaseous constituency and dual phase constituency.

Another object of the invention is to provide a self-contained hand-held cryogenic device which is instantly self-stabilizing to dispense a jet of finely divided liquid coolant.

Another object of the invention is the provision of a cryogenic device for selectively dispensing a stabilized jet of coolant in either single gaseous phase at a temperature above freezing or in a dual phase at a temperature at least as low as −300° F.

Another object of the invention is the provision of a self-pressurized cryosurgery device which is instantly self-stabilizing and effective to dispense a continuous non-varying coolant jet or a readily varied jet of either single or dual phase coolant.

Another object of the invention is the provision of a self-pressurized, self-stabilizing cryogenic device having means for varying the phase consistency of a jet of dispensed coolant by controlling a venting orifice or bleed passage in communication with the space at the entrance end of the jet dispensing orifice.

These and other more specific objects will appear upon reading the following specification and claims and upon considering in connection therewith the attached drawing to which they relate.

Referring now to the drawing in which a preferred embodiment of the invention is illustrated:

FIG. 1 is an elevational view partly in cross-section of one illustrative embodiment of the invention;

FIG. 2 is a fragmentary cross-sectional view on an enlarged scale taken through the upper portion of FIG. 1;

FIG. 3 is a fragmentary view partly in cross-section of the control valve for the venting orifice; and FIG. 4 is a graphical representation of the pressure conditions existing in the expansion chamber for various positions of the throttle valve, the uppermost horizontal line representing the constant coolant reservoir pressure, the middle curve representing the pressure when the venting valve is closed, and the lower curve representing the pressure condition when the venting valve is opened.

Referring initially more particularly to FIG. 1, there is shown an exemplary embodiment of the invention cryogenic device, designated generally 10, when utilizing a dewar flask 11 as a source of heat saturated liquid coolant or cryogen 12. A suitably widely used coolant comprises liquefied nitrogen although it will be understood that any of a considerable number of other liquefied gases having a boiling point of −100° C. or lower, are suitable and may be used in practicing the principles of this invention. Dewar 11 is of generally conventional construction including a stainless steel inner container 13 sealed at its charging inlet 14 to a stainless steel outer evacuated container 15. The tubular neck 16 of the outer container is provided with threads 17 mateable with the threads of a heat insulating lining 18 of the dewar cover or cap 19.

The dispensing and control components of the cryogenic device will be best understood by reference to FIGS. 2 and 3. These components include a main body fitting 20 having a threaded tubular shank projecting downwardly from its lower side and extending through an opening in the top of the dewar cap 19. A threaded bushing 22 is screwed to the lower end of shank 21 and serves to hold the latter firmly assembled to cap 19 along with a thick-walled elastomeric stopper 24 normally closing the tubular dewar charging inlet or opening 25. As is best shown in FIG. 1, stopper 24 has a shoulder seating against the outer rim edge of this inlet. Clamped between the lower end of main body 20 and the top of cap 19 is a curvilinear guard 27 effective to safeguard the user's fingers from contact with the very cold components of the device when in use. Guard 27 may be made of poor heat conductive material, such as stainless steel and includes an upturned tang 28 (FIGS. 1, 3) extending along one sidewall of main body 20.

Supported on the side of main body 20 is a precision valve 30 having a rotary control knob 31 for controlling the position of a throttle or needle valve 32 normally closed against a seat 33. This valve controls the flow of liquid coolant into a tubular expansion housing 35 projecting laterally from the top of main body 20. The lower end of passage 34 is in communication with a tube 36 which is silver-soldered to main body 20 and to a tube 38 extending into close proximity to the bottom of the coolant container 13. Tube 38 is thin-walled brass or stainless steel to present as small a conductive heat path as is practical into the liquid coolant and to assure that failure or breakage of the cryogen dispensing tubes will occur in tube 38 rather than in the inner end of tube 36. This junction between tubes 36 and 38 may be silver-soldered and is located below the threaded tubular extension 21 to simplify replacement and repair of the relatively weak tube 38 should the latter become damaged when cap 19 is disassembled for charging or otherwise. Each of the tubes 36 and 38 is preferably covered with heat insulating material 39, 40 to aid in stabilizing the operation of the apparatus by preventing the flow of liquid coolant through these tubes to cool and condense portions of the coolant vapor present above the liquid level. This could interfere with maintaining a uniform pressure head on the liquid while valve 32 is open and could cause unstable conditions in the jet of coolant before the coolant becomes fully heat saturated.

The dewar is automatically maintained at a predetermined superatmospheric pressure by the vapor pressure of the coolant supply as by a pressure relief valve 43 mounted in the side of main body 20 in communication through passage 44 with the interior of the tubular extension or shank 21. The valve proper 45 of the relief valve is normally held seated against the outlet end of passage 34 by a calibrated spring, not shown, but housed within the valve body. An extension 46 protruding from this valve is readily manipulatable by the operator's finger to unseat the valve and release the pressure in the dewar whenever this is desirable, as before removing cap 19 to renew the supply of coolant 12.

Permanently assembled to the outer end of expansion chamber 35 is a Luer fitting 50 of well known construction providing a readily disconnectable coupling for the shank fitting 51 of a non-pointed or blunt-ended hypodermic needle 52 providing an elongated small bore nozzle or outlet orifice for chamber 35. It will be understood that other outlet orifice constructions can be employed but readily available hypodermic needles having bores ranging in size from 22 to 25 guage have been found highly satisfactory and are quickly and easily substituted for one another to vary the size of the coolant jet dispensed from the expansion chamber. A 22 guage needle has a bore diameter of approximately 17 mils as compared to the 11 mil bore of a guage 25 needle. Needle lengths of ¼" to ¾" are found very satisfactory for use with outlet orifices ranging in size from 11 to 17 mils in diameter. The length of the needle varies with the size of the bleeder orifice. A longer needle necessitates bleeding a greater volume of gaseous phase coolant from the expansion chamber.

A very important further feature of the invention is the provision of means for venting coolant in gas phase from chamber 35 thereby to vary the pressure in chamber 35 relative to the substantially predetermined pressure in the dewar flask without adjusting the flow control valve 30. As herein shown by way of example, this coventing means is provided by tube 54 extending along the interior of chamber 35 with its right-hand end in communication with a passage 55 formed interiorly of body 20. This passage is shown in dot and dash lines and includes a vertical leg and a horizontal leg the latter of which opens to the atmosphere on the left-hand side of the main body 20 (FIG. 3). Normally, the outlet end of passage 55 is closed by a valve 56 mounted on one end of an L-shaped operating lever 57 of poor heat conductive material such as stainless steel. Lever 57 is supported on pivot pins 58 carried by a bracket 59 secured to the side of body 20, and is spring biased by spring 60 to seat the valve 56 against the outlet end of passage 55.

To avoid tolerance problems in the manufacture of the venting orifice or passage, it is found convenient to provide this passage with a loose packing or restrictor to limit the flow of coolant gas allowed to escape to the atmosphere. A very satisfactory restrictor comprises a mass of brass wool or the like here shown as located at the junction of the vertical and horizontal legs of passage 55. Access to this mass 63 is provided by a closure cover 64 to the end that the density of this restrictor may be readily adjusted at the time of manufacture. Thereafter, closure plug 64 may be suitably secured in place since no further adjustment is required so long as the same size pressure relief valve 43 and the same range of sizes of outlet orifice needles 52 are employed.

Referring now to FIG. 4, there is shown a graph depicting typical operating conditions for the cryogenic device herein described when using liquid nitrogen as the coolant and a pressure relief valve calibrated to maintain a pressure of 10 psig. It will be understood that this pressure is merely representative of a pressure found to provide excellent operating characteristics when using outlet passages of the range of sizes described above. This constant pressure condition is represented by the straight horizontal line 65 in FIG. 4. The next lower curve 66 represents the pressure condition within expansion chamber 35 when a 22 guage needle 52 is employed as the jetting orifice as needle valve 32 is opened from its closed to its open position. Curve 67 shows the slightly lower pressure condition created in the expansion chamber when the control lever 57 is depressed to open valve 56 normally closing the venting passage or orifice 55.

Normally the dewar flask is charged with liquid nitrogen and needle valve 32 and venting valve 56 are closed. With the pressure relief valve 43 set, for example, to maintain the pressure within the flask at 10 psig, the coolant will be heat saturated and have a temperature of −312° F. As soon as control knob 31 is operated to open needle valve 32, liquid coolant will rise through conduit 38 and flow past the needle valve whereupon a portion of it will quickly become super-heated as it experiences a pressure drop in flowing past the needle valve into the relatively warm expansion chamber 35. The resulting violent boiling or flashing of the coolant fractionates the liquid into a multiplicity of fine minute particles as other portions convert to the gaseous phase, thereby almost instantly raising the back pressure in the expansion chamber to a value somewhat in excess of one pound less than the internal dewar pressure. Coolant in substantially pure gaseous phase then jets at high velocity from the jetting orifice. A layer of frost also quickly collects on the outer surface of the expansion chamber 35 thereby providing an excellent heat insulating layer for this chamber which greatly minimizes the quantity of coolant going into its gas phase. The cryosurgery device may now be grasped in the operator's hand and manipulated to direct the jet of gaseous coolant onto an area to be sharply cooled.

If the operator wishes to convert the jet to one comprised of finely divided particles of coolant in liquid phase intermixed with gaseous phase coolant, he simply depresses lever 57 to open vent valve 56. Immediately that this takes place the jet converts to a high velocity small diameter jet of dual phase coolant. The conversion occurs substantially instantly, smoothly and in a highly stable manner without need for making any adjustments or change in the position of the needle valve.

Opening of the venting valve is observed to allow a small amount of gaseous phase coolant to be bled from the forward end of the expansion chamber and this is accompanied by a slight drop in the expansion chamber pressure as is clearly evident from a comparison of curves 66 and 67 in FIG. 4. Under the operating conditions depicted, this pressure drop is a small fraction of 1 psi for all positions of throttle valve 32 corresponding to half to fully open position. The volume of coolant issuing from the venting passage 55 is relatively small and completely in gas phase. So long as the venting valve 56 remains open the device continues to operate in the same uniform stable manner irrespective of the position in which the device is held or the manner in which it is manipulated. The coolant jet may be directed at will by the operator in either vertical direction or in any intermediate direction between vertical and horizontal without change in the characteristics of the jet.

Upon release of the pressure on the operating handle 57 of valve 56, this valve recloses cutting off the discharge of gaseous coolant from the venting orifice 55 whereupon the device instantly resumes jetting of gas phase coolant through the jetting orifice. There is no need to make any adjustment of the needle valve.

If the operator wishes to change the size and flow rate of the jet he simply closes valve 32 and detaches needle 51, 52 from the Luer fitting 50 and substitutes a needle of different size.

When the coolant dispenser is not in use, valves 32 and 56 remain closed. Relief valve 43 opens only momentarily at intervals as necessary to maintain the internal pressure of the dewar constant with the result that coolant losses are very small between operating cycles. For example, it is found that a dewar having a charge capacity of approximately one pint is adequate for seven to eight hours of normal usage, or many times longer than prior cryogenic dispensers of similar storage capacity.

While the particular self-pressurizing cryogenic apparatus and method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. In a cryogenic unit, a spray jetting nozzle, a pressure-regulated source of liquid cryogen under substantially uniform pressure, conducting means constantly connecting said source to said nozzle, and manually operable flow control means continuously assembled to said unit and in communication with said conducting means and operable to control the pressure in said conducting means without varying the pressure of said pressure-regulated source of liquid cryogen and effective to cause said cryogen to issue selectively substantially instantaneously from said nozzle as a continuous stable jet of gas or as a continuous stable spray of finely divided liquid particles and gas.

2. The construction defined in claim 1 in which said manually operable means comprise a bleed passage connected to said conducting means, and valve means to open and close said bleed passage to control the escape of gas from said conducting means.

3. The construction defined in claim 1 in which said pressurized liquid cryogen is heat saturated.

4. The construction defined in claim 1 in which said conducting means includes expansion chamber means having an inlet comprising expansion valve means and an outlet comprising said nozzle, and said manually operable means being operatively connected to said expansion chamber means and operable to vary the pressure therein relative to the source pressure of said liquid cryogen.

5. The construction defined in claim 4 in which said expansion chamber means is exposed to the ambient atmosphere.

6. Cryogenic apparatus for producing sub-freezing temperatures comprising:

means including pressure relief valve means providing a source of pressure-regulated liquid cryogen, a spray jetting nozzle, cryogen conducting means connecting said source to said nozzle, and manually operable means to selectively vary the pressure within said cryogen conducting means independently of the pressure of said pressure-regulated source of cryogen and without changing said conducting means thereby to provide substantially instantaneously at the user's option (a) a flow of single phase gaseous cryogen from said nozzle or (b) a spray from said nozzle of dual phase finely divided liquid phase cryogen mixed with gaseous phase cryogen.

7. Cryogenic apparatus as defined in claim 6 wherein said cryogen conducting means includes a cryogen expansion chamber equipped with expansion valve means for admitting pressurized cryogen thereto and having a cryogen outlet connected to said nozzle, and said cryogen pressure varying means comprising normally closed means for bleeding cryogen to the atmosphere from said expansion chamber means and operable when not closed to reduce the cryogen pressure in said expansion chamber means relative to the pressure existing therein when said pressuring varying means is closed.

8. Cryosurgery apparatus for selectively and optionally dispensing a spray of dual phase gaseous and finely divided liquefied cryogen and a jet of substantially single phase gaseous cryogen comprising:

expansion chamber means having a liquid cryogen inlet connected via flow restriction means to a source of pressurized substantially heat saturated liquid cryogen, outlet orifice means for said expansion chamber means, and manually controlled bleed passage means for venting cryogen from the interior of said expansion chamber independently of said outlet orific means and in an amount effective to convert the flow of cryogen from said outlet orifice from a jet of single phase cryogen to a spray of dual phase cryogen containing finely divided particles of liquid cryogen.

9. Cryosurgery apparatus as defined in claim 8 characterized in that said source of pressurized cryogen comprises a dewar flask equipped with pressure relief valve means for storing said heat saturated liquid and maintaining the same pressurized.

10. Cryosurgery apparatus as defined in claim 9 characterized in that said outlet orifice means comprises an elongated small bore passage having a diameter of the order of 11 to 17 mils.

11. Cryosurgery apparatus as defined in claim 10 characterized in that said outlet orifice has a length of the order of 200 to 750 mils.

12. Cryosurgery apparatus as defined in claim 8 characterized in that said manually controlled bleed passage means, when open, has a flow capacity for cryogen in gaseous phase sufficient to lower the pressure in said expansion chamber by a fraction of one psi and under which condition said outlet orifice means is operable to dispense a dual phase jet of finely divided liquefied and gaseous cryogen from said expansion chamber.

13. Cryosurgery apparatus for dispensing a jet of finely divided liquid cryogen comprising:

a source of pressurized cryogen, expansion chamber means having an outlet orifice for pressurized cryogen, means including orifice means for jetting cryogen into said expansion chamber from said pressurized source of liquid cryogen, bleed passage means for venting gaseous cryogen from said expansion chamber to lower the pressure within said chamber sufficiently to provide a steady spray of finely divided liquid cryogen from said outlet orifice, said bleed passage means including means for controlling the flow of gaseous cryogen therethrough and operable to convert the discharge of cryogen from said outlet orifice to gaseous phase cryogen by reducing the flow of gaseous cryogen through said bleed passage means and thereby increasing the pressure in said expansion chamber.

14. Cryogenic apparatus for producing sub-freezing temperatures comprising:

an expansion chamber having an outlet orifice and an inlet orifice provided with cryogen flow control means adapted to be connected to a source of pressurized liquid cryogen maintained substantially at a predetermined pressure, and means connected to said expansion chamber between said inlet and outlet orifices and operable independently of said flow control means for varying the pressure within said expansion chamber relative to the substantially predetermined source pressure of said cryogen thereby to provide substantially instantaneously and at the user's option (a) a sustained flow of gaseous phase cryogen from said outlet orifice or (b) a sustained dual phase spray of finely divided liquid cryogen mixed with gaseous phase cryogen from said outlet orifice.

15. Cryogenic apparatus as defined in claim 14 characterized in that said pressure varying means for converting the flow of cryogen from said outlet orifice between single phase flow and dual phase spray includes bleed passage means for bleeding cryogen from said expansion chamber and including flow control means for said bleed passage.

16. Cryogenic apparatus as defined in claim 15 characterized in that said pressure varying means for converting the flow of cryogen from said outlet orifice between single phase flow and dual phase spray includes manually actuated means independent of said inlet and outlet orifices.

17. Cryogenic apparatus as defined in claim 15 characterized in that said outlet and inlet orifices are located adjacent the opposite ends of said expansion chamber.

18. Cryogenic apparatus as defined in claim 17 characterized in that said pressure varying means for converting the flow of cryogen from said outlet orifice between single and dual phase flow includes manually controllable means for bleeding cryogen from an interior portion of said expansion chamber adjacent said outlet orifice.

19. Cryogenic apparatus as defined in claim 14 characterized in that said pressure varying means for converting the flow of cryogen from said outlet orifice between single phase flow and dual phase spray includes bleed passage means in communication with the interior of said expansion chamber and opening to the atmosphere and equipped with flow regulating valve means.

20. Cryogenic apparatus as defined in claim 19 characterized in the provision of means normally holding said valve means closed and thereby effective to maintain the pressure in said expansion chamber slightly higher than when said valve means is open and under which closed valve conditions only single phase cryogen flow issues from said outlet orifice.

21. Cryogenic apparatus as defined in claim 14 characterized in that said expansion chamber is mounted on a removable closure for the inlet of a dewar chargeable with liquid cryogen and includes means for supplying pressurized cryogen from said dewar to said inlet orifice.

22. Cryogenic apparatus as defined in claim 21 characterized in that said means for supplying pressurized cryogen to said inlet orifice comprises a tube of heat insulating material.

23. A cryogen dispensing device comprising:
a hand-held dewar having an inlet provided with a removable closure, cryogen expansion chamber means having a cryogen dispensing orifice and a cryogen inlet and expansion orifice, heat insulated means within said dewar supplying liquid cryogen to said expansion orifice under pressure, and controllable bleed passage means for bleeding sufficient cryogen from said expansion chamber means to lower the pressure therein sufficiently to convert the discharge of pressurized cryogen from said dispensing orifice from single phase gaseous cryogen to dual phase spray of gas and finely divided liquid phase cryogen.

24. A cryogen dispensing device as defined in claim 23 wherein said controllable bleed passage means includes flow control means operable independently of said inlet and dispensing orifices to vary the pressure in said expansion chamber while said inlet orifice is in a normal open operating position thereby to convert the dispensed cryogen between single phase flow and dual phase spray.

25. A cryogen dispensing device as defined in claim 23 wherein said controllable bleed passage means includes a normally closed valve.

26. A cryogen dispensing device as defined in claim 23 wherein said expansion chamber means is carried by said dewar closure and wherein said expansion orifice includes a needle valve located on the exterior of said dewar closure.

27. A cryogen dispensing device as defined in claim 23 wherein said device is provided with a pressure relief valve.

28. A cryogen dispensing device as defined in claim 27 wherein said relief valve is manually manipulatable to release the pressure of the dewar when charged with cryogen and prior to detaching said closure.

29. That method of preventing the entrance of atmospheric air and foreign matter into the cryogen jetting nozzle of cryosurgery apparatus between intervals of nonuse of the apparatus to spray dual phase gaseous and liquid cryogen onto tissue to necrotize the same which method comprises:
providing a cryogen expansion chamber with a cryogen discharge nozzle and an independent gas vent to the atmosphere;
expanding pressurized cryogen into said expansion chamber with said gas vent closed sufficiently to maintain the cryogen pressure in said expansion chamber at a first relative high value such that substantially single phase gaseous cryogen flows from said discharge nozzle; and
opening said gas vent sufficiently to reduce the cryogen pressure in said expansion chamber to a second and lower value and thereby effective to discharge cryogen from said discharge nozzle in dual phase comprising finely divided liquid and gaseous phase cryogen for use in low temperature tissue necrotizing operations.

30. That improved method of quickly forming a stabilized cryogen jet containing a mixture of gaseous phase and minute particles of liquid phase cryogen from a pressurized heatsaturated liquid supply thereof which comprises:
passing liquefied cryogen from said pressurized supply into a chamber under conditions permitting a portion of the cryogen to vaporize, dispensing a jet containing minute particles of liquid phase cryogen intermixed with gaseous phase cryogen from said chamber onto a selected surface area of an object to quickly lower the temperature of said surface area while bleeding another portion of the cryogen to the atmosphere from said chamber, and interrupting the step of bleeding said portion of cryogen to the atmosphere to convert the dual phase cryogen jet dispensed from said expansion chamber to a single phase cryogen jet.

31. That improved method defined in claim 30 characterized in the step of controlling the relative proportions of cryogen in gaseous and liquid phase comprising said dispensed jet of cryogen by bleeding gaseous phase cryogen from said chamber to the atmosphere at a selected rate ranging between zero and a rate providing a maximum proportion of liquid phase cryogen in said dispensed jet of cryogen.

32. That improved method of dispensing a jet of cryogen fluid onto a surface to be sharply cooled which comprises:

expanding pressurized substantially heat saturated cryogen into a chamber, providing said chamber with an outlet orifice, and selectively jetting cryogen from said outlet orifice in (a) dual phase gaseous and finely divided liquid state and in (b) single phase gaseous state by bleeding to the atmosphere a fractional portion of the cryogen flowing toward said outlet orifice to obtain dual phase flow from said outlet orifice and bleeding substantially no portion of the cryogen to the atmosphere while en route to said outlet orifice to obtain single phase flow from said outlet orifice.

33. A cryogenic spray unit comprising:

a source of cryogenic fluid equipped with means to maintain the same under substantially uniform pressure, a nozzle and conducting means to conduct said cryogenic fluid from said source to said nozzle including manually operable means connected to said conducting means between the inlet thereof and said nozzle to control the flow in said conducting means to cause said flow to issue from said nozzle into the atmosphere selectively as a gas or as a mixture of gas and fluid particles.

34. The construction recited in claim 33 characterized in that said means to cause said fluid to issue selectively as a gas or as a mixture of gas and fluid particles comprises manually controlled valve means to control the flow of cryogenic fluid from said source and manually controlled means connected to said conducting means to vary the pressure of the fluid at the entrance of said nozzle.

35. A cryosurgical apparatus for spraying cryogenic fluid comprising:

a source of cryogenic fluid under pressure, a nozzle adapted to discharge a small flow of single phase gas or a two phase mixture of gas and fine liquid particles into the atmosphere, and conveying means constantly assembled to said nozzle to convey said fluid from said source to said nozzle including manually controlled means continuously connected to said conveying means and operable to vary the pressure in said means to convey to selectively cause said fluid to discharge from said nozzle into the atmosphere as a gas or as a mixture of gas and liquid particles.

36. Cryogenic apparatus for dispensing a jet of dual phase cryogen onto tissue to necrotize the same comprising:

a container for storing a quantity of pressurized liquified cryogen;

cryogen expansion chamber means in communication with a supply of liquefied cryogen in said container via cryogen flow restrictor means; and said expansion chamber means having a bleed orifice and a jetting orifice wherein said bleed orifice is equipped with openable and closeable flow control means for venting only gaseous cryogen to the atmosphere at any time, said control means controlling flow from said bleed orifice thereby controlling the phase of the flow from said jetting orifice and wherein said jetting orifice is selectively operable to jet only gaseous cryogen when said flow control means is closed and to jet particles of liquid cryogen intermixed with gaseous cryogen therefrom on to tissue to be necrotized when said flow control means is open.

37. Cryogenic apparatus as defined in claim 36 characterized in that said container is a dewar flask having a removable closure for a cryogen charging opening, said expansion chamber means being mounted on the exterior of said removable closure.

38. Cryogenic apparatus as defined in claim 37 characterized in the provision of pressure relief valve means for limiting the pressure interiorly of said container when charged with cryogen.

39. Cryogenic apparatus for use in necrotizing tissue comprising:

means for storing a supply of pressurized liquefied cryogen;

expansion chamber means in communication with said liquefied cryogen via flow restrictor means; and said expansion chamber having first orifice means for venting only gaseous cryogen to the atmosphere from said expansion chamber at any time and second orifice means operable so long as said first orifice means is open for spraying a stream of dual phase cryogen onto tissue to be necrotized which stream comprises gaseous cryogen intermixed with particles of liquid cryogen.

40. Cryogenic spray apparatus as defined in claim 39 characterized in the provision of valve means for controlling the flow of gaseous cryogen vented to the atmosphere through said first orifice means.

41. Cryogenic spray apparatus as defined in claim 39 characterized in the provision of flow control means for controlling flow through said first orifice means and operable to convert the flow of cryogen through said second orifice means between a flow of gaseous cryogen only and an intermixed flow of gaseous and finely divided liquid cryogen.

42. In a cryogenic unit, a nozzle, a source of pressurized liquid cryogen, conducting means connecting said source to said nozzle and including an expansion chamber at the end thereof connected to said nozzle, and means including flow limiting means connected to the interior of said expansion chamber for venting cryogen to the atmosphere in a flow path by-passing said nozzle and effective to assure a discharge from said nozzle of a spray of finely divided liquid cryogen and gaseous cryogen substantially immediately upon the initiation of flow of cryogen into said expansion chamber and the venting of cryogen to the atmosphere via said flow limiting and venting means, and means operable to control the passage of cryogen to the atmosphere via said flow limiting and venting means.

43. The construction defined in claim 42 characterized in that said flow limiting and venting means is connected to the interior of said expansion chamber in an area near the entrance to said nozzle.

44. The construction defined in claim 42 characterized in that said flow control means is manually manipulatable to convert the discharge of cryogen from said nozzle substantially instantaneously between a flow of single phase gaseous cryogen and a flow of dual phase gaseous and finely divided particles of liquid cryogen.

* * * * *